US00PP14504P29

(12) United States Plant Patent
van der Kraan-Zonderland

(10) Patent No.: US PP14,504 P2
(45) Date of Patent: Feb. 3, 2004

(54) GYPSOPHILA PLANT NAMED 'BLANCANIEVES'

(50) Latin Name: *Gypsophila hybrida*
Varietal Denomination: Blancanieves

(75) Inventor: Maria Francisca Theresia van der Kraan-Zonderland, Delft (NL)

(73) Assignee: Astee Flowers B.V., Nieuwveen (NL)

( * ) Notice: Subject to any disclaimer, the term of this patent is extended or adjusted under 35 U.S.C. 154(b) by 0 days.

(21) Appl. No.: 10/303,495

(22) Filed: Nov. 25, 2002

(51) Int. Cl.[7] ..... A01H 5/00
(52) U.S. Cl. ..... Plt./354
(58) Field of Search ..... Plt./354

*Primary Examiner*—Bruce R. Campell
*Assistant Examiner*—June Hwu
(74) *Attorney, Agent, or Firm*—C. A. Whealy

(57) ABSTRACT

A distinct cultivar of Gypsophila plant named 'Blancanieves', characterized by its upright plant habit; freely flowering habit; many-petaled white-colored flowers arranged in compound cymes; and good post-production longevity.

1 Drawing Sheet

Botanical classification/cultivar designation: *Gypsophila hybrida* cultivar Blancanieves.

BACKGROUND OF THE INVENTION

The present Invention relates to a new and distinct cultivar of Gypsophila plant, botanically known as *Gypsophila hybrida,* grown commercially as a cut flower, and hereinafter referred to by the name 'Blancanieves'.

The new Gypsophila is an induced mutation of an unidentified proprietary selection of *Gypsophila hybrida,* not patented. The proprietary selection is the product of a open-pollination of *Gypsophila hybrida* Iron Gypsophila as the female, or seed, parent, not patented, and an unknown cultivar as the male, or pollen parent. Cuttings from chemically treated plants were planted and the new Gypsophila was discovered and selected by the Inventor in 1998 in a controlled environment in Delft, The Netherlands, as a single flowering plant among a population of plants. Plants of the new Gypsophila differed from plant of the proprietary selection in flower size and inflorescence form.

Asexual reproduction of the new Gypsophila by cuttings taken at Delft, The Netherlands, has shown that the unique features of this new Gypsophila are stable and reproduced true to type in successive generations.

SUMMARY OF THE INVENTION

The following traits have been repeatedly observed and are determined to be the unique characteristics of 'Blancanieves'. These characteristics in combination distinguish 'Blancanieves' as a new and distinct cultivar:

1. Upright plant habit.
2. Freely flowering habit.
3. Many-petaled white-colored flowers arranged in compound cymes.
4. Good post-production longevity.

In side-by-side comparisons conducted in Delft, the Netherlands, plants of the new Gypsophila have larger flowers and a more open inflorescence form than plants of Iron Gypsophila. In side-by-side comparisons conducted in Delft, the Netherlands, plants of the new Gypsophila have shorter leaves, smaller flowers with more petals, stronger flower stems, and more erect and compact inflorescences than plants of the cultivar Magic Golan disclosed in U.S. Plant Pat. No. 9,257.

Plants of the new Gypsophila can be compared to plants of the cultivar Dangypmini, disclosed in U.S. Plant Pat. No. 10,964. In side-by-side comparisons conducted in Delft, The Netherlands, plants of the new Gypsophila are more outwardly spreading, have lighter green-colored leaves, and have larger flowers with more petals per flower. In addition, plants of the new Gypsophila do not have stamens whereas plants of the cultivar Dangypmini have stamens.

Plants of the new Gypsophila differ from plants of the Gypsophila cultivar Summer Snow, disclosed in a U.S Plant patent application Ser. No. 10/303,438 filed concurrently, in plant habit as plants of the cultivar Summer Snow are more compact and typically grown as potted plants.

The cultivar Blancanieves has not been observed under all possible environmental conditions. The phenotype may vary somewhat with variations in environment such as temperature and light intensity, without, however, any variance in genotype.

BRIEF DESCRIPTION OF THE PHOTOGRAPH

The accompanying colored photograph illustrates the overall appearance of the new Gypsophila, showing the colors as true as it is reasonably possible to obtain in colored reproductions of this type. Colors in the photograph may differ slightly from the color values cited in the detailed botanical description which accurately describe the colors of the new Gypsophila. The photograph comprises a side perspective view of a typical cut flower stem of the new Gypsophila.

DETAILED BOTANICAL DESCRIPTION

In the following description, color references are made to The Royal Horticultural Society Colour Chart, 2001 Edition, except where general terms of ordinary dictionary significance are used. The aforementioned photograph, following observations and measurements describe one-year old plants grown as cut flowers during the summer in Poeldijk, The Netherlands, in a glass-covered greenhouse with day temperatures about 15° C. and night temperatures about 10° C.

Botanical classification: *Gypsophila hybrida* cultivar Blancanieves.

Commercial classification: Cut flower Gypsophila.

Parentage: Induced mutation of an unidentified proprietary selection of *Gypsophila hybrida,* not patented.

Propagation:

*Type.*—By cuttings.

*Time to initiate roots.*—Summer: About 21 to 30 days at a temperature of 22° C. Winter: About 26 to 34 days at a temperature of 18° C.

*Root description.*—Fine and well-branched.

Plant description:

*Appearance.*—Perennial cut flower. Stems upright; broadly inverted triangular form. Freely flowering; white-colored flowers with numerous petals per flower arranged in compound cymes.

Moderate to vigorous growth habit.

*Branching habit.*—Freely basal branching; about eight flowering stems per plant are produced per year.

*Plant height.*—About 105 cm.

*Plant width.*—About 90 cm.

*Lateral branch length.*—About 85 cm.

*Lateral branch diameter.*—About 3.5 mm.

*Internode length.*—About 2.2 cm.

*Strength.*—Strong.

*Stem texture.*—Glabrous.

*Stem color.*—138B.

*Foliage description.*—Arrangement: Opposite; sessile. Shape: Narrowly elliptic to narrowly lanceolate. Apex: Acute. Base: Cuneate. Margin: Entire. Length: About 6.3 cm. Width: About 1.3 cm. Texture: Glabrous; slightly leathery. Venation pattern: Parallel. Color: Young leaves, upper surface: Between N189A and N189B. Young leaves, lower surface: 189A. Fully expanded leaves, upper surface: Slightly darker than 189A. Fully expanded leaves, lower surface: 137B. Venation, upper surface: Between N189A and N189B. Venation, lower surface: 143A.

Flowering description:

*Appearance.*—Upright compound cymes with numerous many-petalled white-colored flowers, flowers rotate; about 250 flowers per inflorescence. Flowers face upright to slightly outwardly.

*Flowering response.*—Under outdoor conditions, plants flower from July through October.

*Post-production longevity.*—Good; flowers last about 10 days. Inflorescences persistent.

*Fragrance.*—Faint; sweet.

*Inflorescence length.*—About 25 cm.

*Inflorescence width.*—About 16 cm.

*Inflorescence bud.*—Shape: Flattened globular. Length: About 3 mm. Diameter: About 3 mm. Color: 157D.

*Flower diameter.*—About 7 mm.

*Flower depth (height).*—About 5 mm.

*Petals/petaloids.*—Quantity per flower: About 25. Shape: Oblanceolate. Apex: Praemorse. Base: Attenuate. Margin: Entire. Length: About 4 mm. Width: About 2 mm. Texture: Smooth, glabrous. Color: When opening, upper and lower surfaces: Close to 155D; towards the base, 143D. Mature, upper and lower surfaces: Close to 155D; towards the base, 143D; color becoming closer to 199D with development.

*Sepals.*—Quantity per flower: About five. Shape: Elliptic. Apex: Acute. Base: Cuneate. Margin: Entire. Length: About 2 mm. Width: About 1 mm. Color: Immature and mature, upper surface: 141B. Immature and mature, lower surface: 137C.

*Peduncle.*—Strength: Strong. Length: About 2.2 cm. Diameter: About 1 mm. Angle: About 10 to 40° from vertical. Texture: Smooth. Color: 143A.

*Pedicels.*—Strength: Moderately strong. Length: About 8 mm. Diameter: About 0.3 mm. Angle: About 10 to 40° from vertical. Texture: Smooth. Color: 143A.

*Reproductive organs.*—Stamens: None observed, all transformed into petaloids. Pistils: Quantity per flower: About two. Style length: About 3.45 mm. Style color: 157B to 157C. Pistil length: About 3.5 mm. Stigma color: 157C to 157D. Ovary color: 143A to 143B.

*Seed/fruit development.*—Seed and fruit development has not been observed.

Disease/pest resistance: Plants of the new Gypsophila have not been observed to be resistant to pathogens and pests common to Gypsophilas.

It is claimed:

1. A new and distinct cultivar of Gypsophila plant named 'Blancanieves', as illustrated and described.

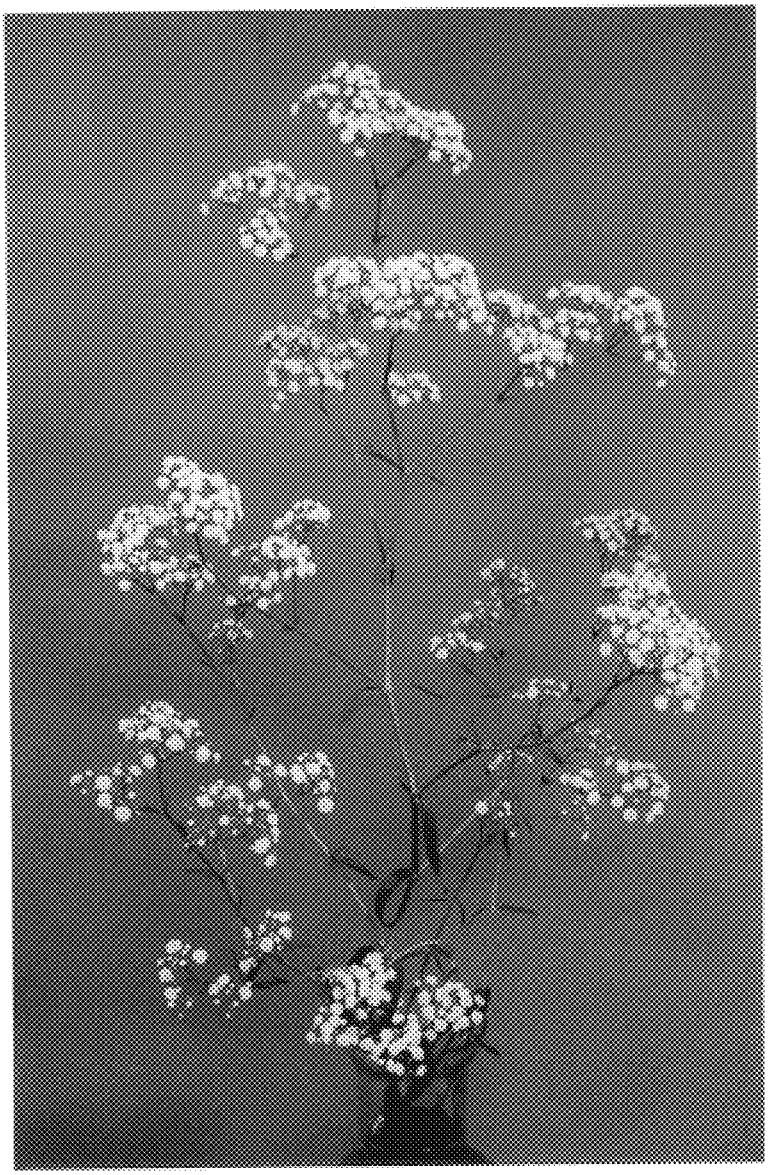

* * * * *